United States Patent [19]

Sacks

[11] 4,202,347
[45] May 13, 1980

[54] METHOD AND APPARATUS FOR DETERMINING BLOOD PRESSURE

[76] Inventor: Alvin H. Sacks, 12682 Roble Veneno, Los Altos Hills, Calif. 94022

[21] Appl. No.: 841,241

[22] Filed: Oct. 11, 1977

Related U.S. Application Data

[63] Continuation-in-part of Ser. No. 750,077, Dec. 13, 1976, abandoned, which is a continuation-in-part of Ser. No. 584,102, Jun. 5, 1975, abandoned.

[51] Int. Cl.$^2$ ............................................. A61B 5/02
[52] U.S. Cl. ............................................. 128/677; 128/686
[58] Field of Search ................. 128/2.05 A, 2.05 C, 128/2.05 G, 2.05 M, 2.05 N, 2.05 P, 2.05 Q, 2.05 R, 2.05 T, 2.05 V, 327

[56] References Cited

U.S. PATENT DOCUMENTS

| | | | |
|---|---|---|---|
| 598,343 | 2/1898 | Hill et al. | 128/2.05 G |
| 1,188,748 | 6/1916 | Fosgate | 128/2.05 G |
| 1,900,285 | 3/1933 | Huber | 128/2.05 N |
| 2,753,863 | 7/1956 | Bailey | 128/2.05 G |
| 3,482,565 | 12/1969 | Gowen | 128/2.05 A |
| 3,504,663 | 4/1970 | Edwards | 128/2.05 G |
| 3,837,347 | 9/1974 | Tower | 128/419 P |

FOREIGN PATENT DOCUMENTS 42276   4/1933   France ............................. 128/2.05 G Primary Examiner—William E. Kamm
Attorney, Agent, or Firm—Julian Caplan

[57] ABSTRACT

It has been found that most subjects can sense the onset and cessation of the conditions in a blood vessel which give rise to the Korotkoff sounds used in blood pressure determination without use of a stethescope or any transducer and thus adequately read their own blood pressure using the blood pressure device. An inelastic cuff encircles a thumb or other portion of the subject's body and contains a diaphragm which is inflatable. A syringe-like member is connected to the diaphragm. Indicia on the barrel in accordance with the Perfect Gas Law indicate pressure at the onset and cessation of localized arterial sensations corresponding to Korotkoff sounds to afford readings of diastolic and systolic pressures. Zeroing of the indicia is provided to accommodate different sizes of thumbs, etc.

25 Claims, 17 Drawing Figures

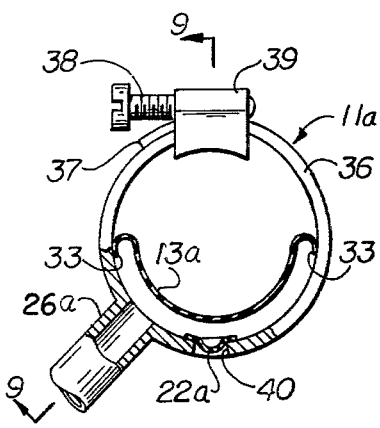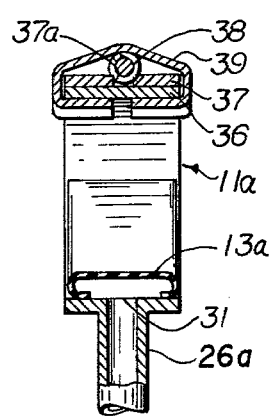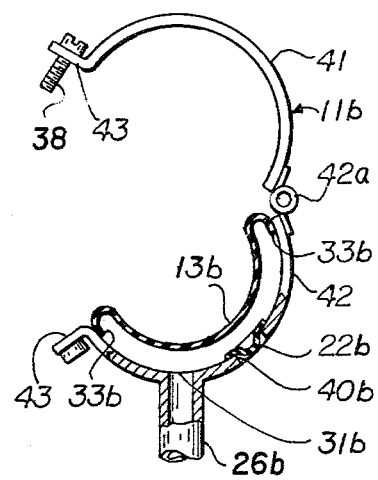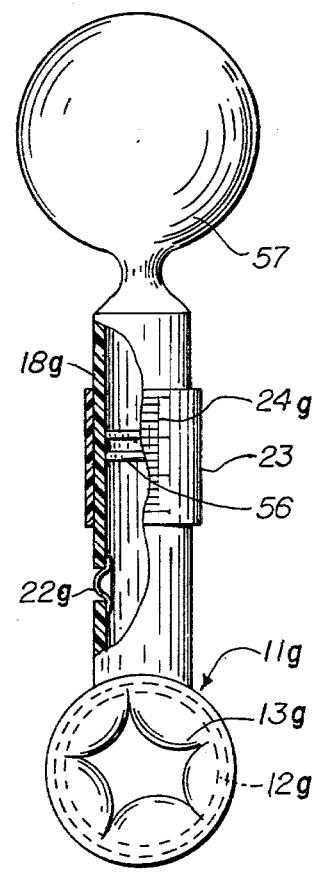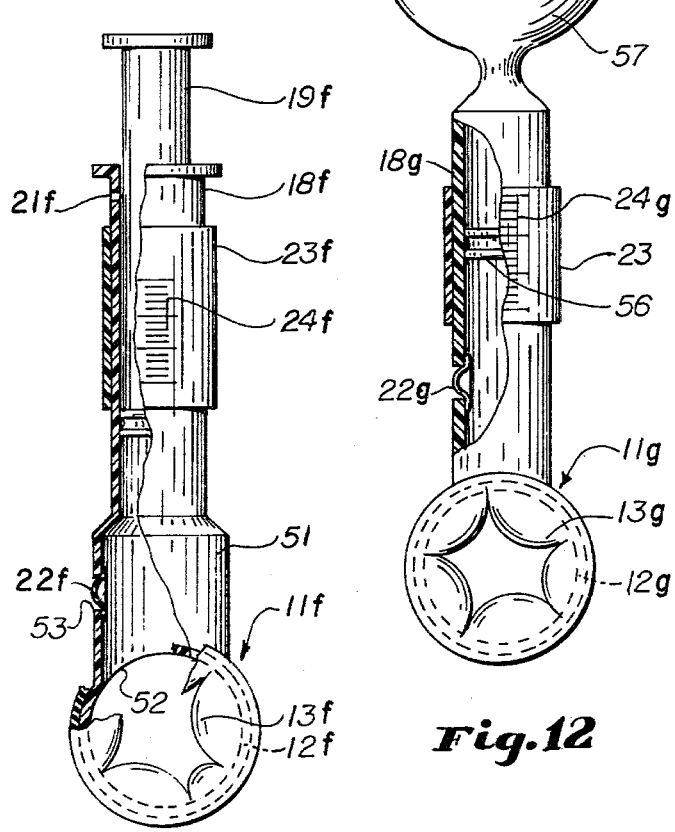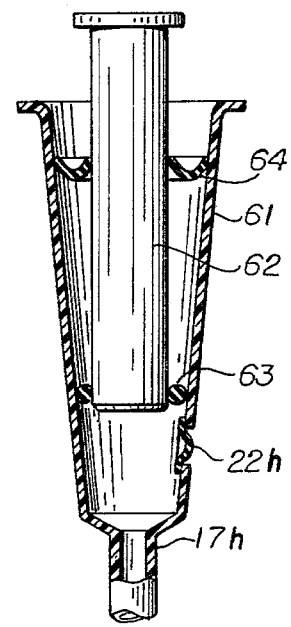

METHOD AND APPARATUS FOR DETERMINING BLOOD PRESSURE

This is a continuation-in-part of U.S. Ser. No. 750,077 filed Dec. 13, 1976, now abandoned, which was a continuation-in-part of U.S. Ser. No. 584,102 filed June 5, 1975, now abandoned.

This invention relates to a new device for determining blood pressure without the use of a stethoscope or transducer. More particularly, the invention relates to a cuff which may be placed around a finger, thumb, wrist or any other extremity of the body containing an artery and which cuff can be inflated to perform a function analogous to that of the standard cuff used in all sphygmomanometers. The cuff may be inflated in various ways, for example, by means of a cylinder having a plunger resembling a large syringe. Since the pressure in the cuff is related to the volume of the air expelled from the syringe, a pressure reading is obtainable.

It has been found that the average person can sense the onset and cessation of conditions which are ordinarily detected by auscultation, conventionally by the use of a stethoscope, to determine both systolic and diastolic readings of pressure.

By using a cuff and chamber of this invention and by eliminating the transducer or even a stethoscope, a simplified device wherein a person can determine his own blood pressure is provided.

The present invention simplifies the equipment required to determine blood pressure in two principal respects. In the first place, the manometer, be it the mercury column type or the aneroid type, is replaced with a manually operated volume control which is much less fragile, less expensive and more easily used by the patient. In the second place, the transducer or stethscope is eliminated because the person's own sensations in the finger or other extremity are used to determine the time at which the systolic or diastolic pressure reading is to be taken.

The development of modern blood pressure measurement is attributed primarily to two individuals. The first important advance was in 1896 by Riva Rocci who invented an inflated pneumatic cuff for the upper arm used to obliterate the pulse at the wrist. The second advance was in 1905 by Korotkoff who suggested that the sounds heard over the artery just distal to the cuff should be used as indices of systolic and diastolic pressure. Since 1905, there has been considerable refinement and automation of equipment, but, nevertheless at the present time, blood pressure is ordinarily determined by a physician or trained technician employing an inflatable cuff, usually attached to the upper arm, and a stethoscope placed over an artery below the cuff. Alternatively, the physician's function is sometimes performed by autoomated equipment and the stethoscope is replaced by a microphone or transducer. In any case, the cuff is inflated until circulation through the artery is stopped; then the pressure is gradually reduced and the pressure on the manometer noted (or recorded) when the first sound is detected corresponding to the systolic pressure, and then the pressure reading on the manometer is noted when the last sound disappears (or fades) corresponding to diastolic pressure.

The present invention is based on a new concept which is that the subject can sense said arterial sensation of the phenomenon of his blood flow which is responsible for producing the Korotkoff sounds. Hence the need for a stethoscope or transducer is eliminated and the person merely measures the points in a range of pressures at which the localized sensations in the artery begin and subside as applied pressure is increased or decreased.

It is important to point out that the Korotkoff sounds are localized arterial sensations which must not be confused with other "throbbing" or "pulsing" sensations noted during pressurization of the subject's extremity. The localized sensations in the artery are associated with the Korotkoff sounds. The generalized throbbing sensations felt at pressures above systolic (usually above the cuff) are related to pumped blood being unable to enter the vessels covered by the cuff.

In the method of the invention, the sensations at systolic cuff pressure are within the cuff and, in the arm, are felt very locally in the brachial artery. Additionally, a general rhythmic swelling sensation of the whole member or extremity may be felt during pressurization (particularly in the finger at cuff pressures below diastolic), which is again unrelated to the Korotkoff sensations and is not confined to the artery. The early researchers of digital blood pressure failed to recognize the close relationship between the specific Korotkoff sensations of the subject and blood pressures. They were able to take only erratic and unreliable diastolic digital pressure readings by cuff pressurization of digits. They failed to distinguish between the true Korotkoff sensations and the non-Korotkoff associated throbbing sensations just discussed,, which failure lead to erroneous pressure readings. Based on their results, they even stated that subjective "sensations" were not consistently reliable to determine blood pressures.

In the method which is based solely upon the Korotkoff phenomenon, a subject can easily detect, in the range of cuff pressure between systolic and diastolic, the distinctly localized arterial sensations felt inside the cuff, which are associated with this phenomenon, and thereby obtain consistent and reliable readings of both systolic and diastolic blood pressures.

Another simplification accomplished by the present invention is the replacement of manometric pressure measurement with measurement of the volume change of gaseous fluid required to produce that pressure. This is accomplished by making use of the perfect gas law and observing that the process of the present invention is an isothermal one (i.e., the temperature remains constant). The gas law states that the pressure varies inversely with the volume. Therefore, the measured volume change can be calibrated in terms of pressure change and thus used to determine the pressure.

Another feature of the invention is the "zeroing" of the system, using a flexible diaphragm or popout valve which is activated when subjected to pressure, by adjusting a pressure scale so that the zero is properly adjusted to the particular digit being tested. It will be understood that the size of the finger, thumb or limb varies from one person to another, and since the measurement of pressure is being gauged by change in volume, it is important that there be a zero adjustment for the particular limb being used. In accordance with the present invention, a simplified means for zero adjustment is provided, the means cooperating with indicia for volume or pressure.

The device of the invention thus comprises a cuff which encircles a portion of the person's body containing an artery, the cuff includes a casing and a diaphragm inside of the casing to engage said body portion, said diaphragm being inflatable against said body portion to effect in the person a localized throbbing sensation in the artery; wall means including the casing and diaphragm defining the walls of a chamber which confine a gaseous fluid to inflate the diaphgram; a control means cooperating with the chamber so as to vary the total volume of the chamber, and so vary the fluid pressure against the diaphragm. The control means is in cooperation with an indicator means which indicates differences in volume of the chamber between a base volume, at which the diaphragm firmly engages the body portion without affecting blood flow through the artery, and the highest and lowest volumes at which the subject feels a localized throbbing sensation in the artery, the indicator means thereby providing indications of diastolic and systolic blood pressure at the highest and lowest volumes, respectively. The indicator means includes a scale calibrated to indicate pressure in response to volume changes in the chamber. The device may further include a means for indicating when base volume is reached and a means for adjusting the indicator means to provide a reading of such base volume, herein referred to as "zeroing". Actually, "zero" may correspond to a small known pressure.

The accompanying drawings, in which similar characters of reference represent corresponding parts in each of the several views, illustrate various embodiments of the device of the invention.

In the drawings:

FIG. 8 is a view similar to FIG. 3A of a further modification.

FIG. 9 is a section taken substantially along the line 9—9 of FIG. 8.

FIG. 10 is a view similar to FIG. 3A of still another modification.

FIG. 11 is an end elevational view of a still further modification of the structure of FIG. 1 partly broken away in section.

FIG. 12 is an end elevational view of still another modification to FIG. 1 partly broken away in section.

FIG. 13 is a view similar to FIG. 1 broken away in section of a still further modification.

The perfect gas law is as follows:

$$pV = RT$$

$$\text{Log } p + \text{Log } V = \text{Log } R + \text{Log } T$$

$$dp/p + dV/V = dT/T$$

if $dT = 0$, then $$dp/p = -dV/V$$

Hence a 1% reduction in the overall gas volume of the system by compressing the plunger would produce a cuff pressure of 1% of one atmosphere or 7.6 mm Hg. at sea level. If the chamber is inelastic, then the overall change in volume is just the volume displaced by the plunger. Otherwise, the compliance of the various components affects V and may be accounted for by calibration of the system.

The foregoing principle is applied to the present invention for monitoring blood pressure. The resulting relationship between pressure and volume is not quite linear but is determined for the particular device either from the above equations or by a one-time calibration against a manometer or by a combination of both.

Figure 1:
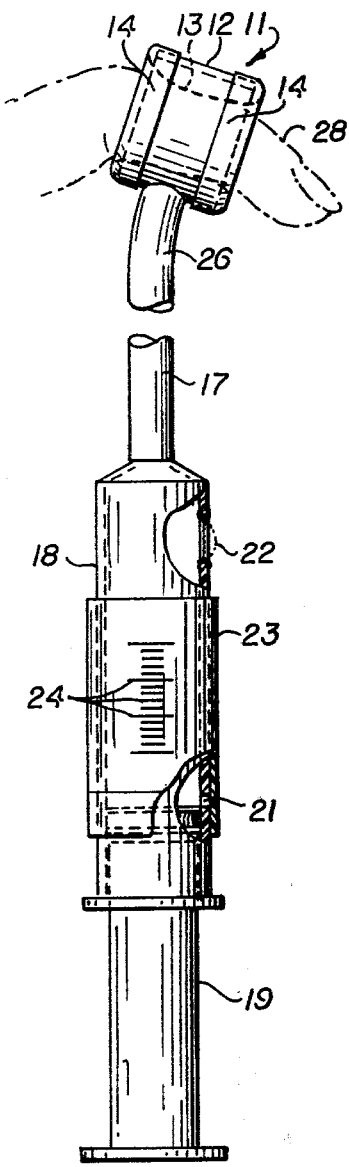
FIG. 1 is an elevational view, partly broken away in section and to reduce size, showing a device in accordance with the present invention as applied to the finger of the user.
Figure 2:
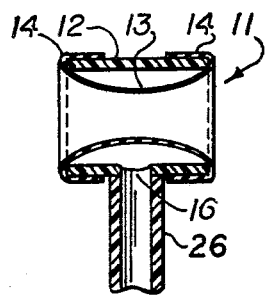
FIG. 2 is a sectional view through a portion of the structure of FIG. 1.

In FIGS. 1 and 2, a cuff 11 is provided dimensioned to fit over the finger 28, wrist, arm or other extremity of the body containing an artery. Cuff 11 has an inelastic casing 12, and in the interior thereof is a tubular diaphragm 13, the ends 14 of which are brought around the outside of casing 12 and secured thereto by cement, bands (not shown) or other means. The relaxed diaphragm 13 is sufficiently large to conveniently fit over the finger 28.

In FIG. 1, which illustrates the use of a tubular member, such as cylinder 18, and plunger device (conventionally used in injections, but preferably of such volume and diameter to afford accurate volume determinations in accordance with the above equations) as the control means cooperable with the casing and diaphragm, an opening 16 is formed in casing 12 on the outside of diaphragm 13 and connects by duct means 26 to an inelastic, flexible tube 17, which is fixed to the closed end of cylinder 18. The plunger 19 fits in fluid tight relation to the internal wall of cylinder 18.

Figure 4:
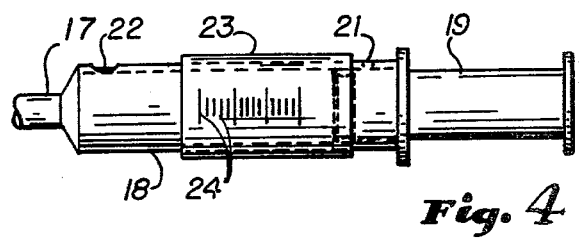
FIG. 4 is a fragmentary elevational view showing the pressure scale in one position and the plunger retracted.
Figure 5:
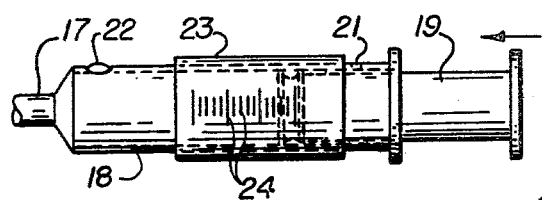
FIG. 5 is a view similar to FIG. 4 showing the plunger partly retracted.

In FIG. 1, in order to make it possible to insert plunger 19 into the cylinder 18 without inflating the diaphragm, a small hole or vent 21 is formed in the wall of cylinder 18. At the end of the cylinder 18 adjacent to tube 17 is a "zero-indicating" device which consists of a small aperture closed by a valve-like member 22 formed of a flexible piece of material so that when pressure is applied inside cylinder 18 the member 22 bulges outwardly (compare FIG. 5 with FIG. 4) indicating that there is a slight pressure on the inside of diaphragm 13. This pressure may be determined by measuring once with a manometer or other conventional means.

Movable on the outside of cylinder 18 is a scale 23 formed with indicia 24 indicating pressure.

Figure 7:
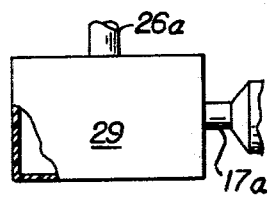
FIG. 7 is a fragmentary elevational view of the plenum chamber partly broken away in section.
Figure 6:
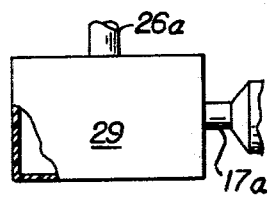
FIG. 6 is a view similar to FIG. 5 showing the scale adjusted for "zero".

In FIG. 7, a rigid plenum chamber 29 may be interposed between tube 17a of the cylinder 18 and tube 26a which communicates with the cuff. By including the volume of the plenum chamber in the total volume of the system, greater sensitivity is achieved in accordance with the equations.

In the use of the device as shown, with the diaphragm relaxed, the cuff 11 is slipped over the finger as shown in FIG. 1. If the plunger 19 has not previously been inserted in the cylinder 18, that is then done, air escaping through vent 21 until the end of the plunger closes off the vent 21.

Figure 15:
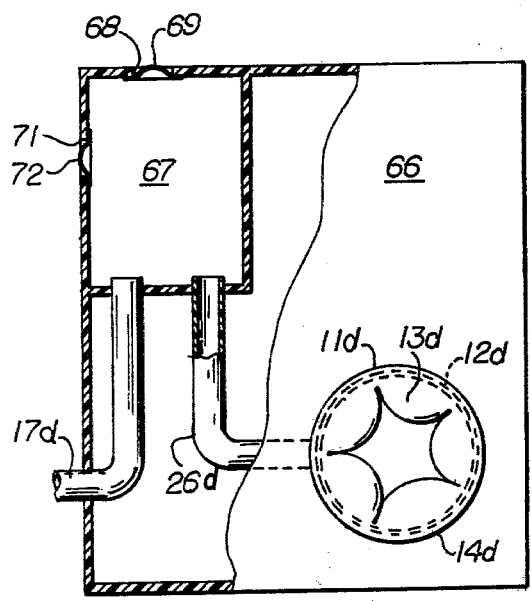
FIG. 15 is an end elevational view partly broken away in section to reveal internal construction showing a container in which portions of a device, in accordance with the present invention, are installed.

As has previously been expressed, the size of finger 28 or other extremity varies with the user. It is important to the determination of "zero" pressure to be able to observe when inflated diaphragm 13 is in firm engagement with the skin of the finger but pressure has not been applied which affects the flow of the blood through the artery. For this purpose, the member 22 is observed. When the number first distends from the relaxed position of FIG. 4 to the distended position of FIG. 5, then the cuff is in firm engagement with finger 28. This point is noted and the sliding scale is adjusted in position so that the "zero" marking is opposite the then position of the inner end of the plunger 19. In this connection, it is to be understood that since the invention relies on the perfect gas law, any air leak from the chamber would alter the pressure-volume relationship and therefore result in erroneous pressure readings. Accordingly, a pressure-responsive means may be provided which will automatically alert the user to any such leak during the use of the device. This means can consist of a second valve-like member, in addition to that used for zeroing, which is activated at a higher predetermined pressure. In FIG. 15, which shows a plenum chamber 67 integrated with a casing 12d and a diaphragm 13d, one valve-like member 69 is for "zero-indicating", while the second valve-like member 27 is for leak detection. Thus, after the user has zeroed the device, if the second valve-like member does not pop out when the control means has pressurized the device to a position indicating the predetermined pressure, a leak must be present in the system. The second valve-like member can be made, for example, of a stiffer material than that used for the "zero-indicating" valve-like member, and the pressure required to activate it can be determined by a one-time calibration against a mercury manometer or other pressure gauge.

Figure 14:
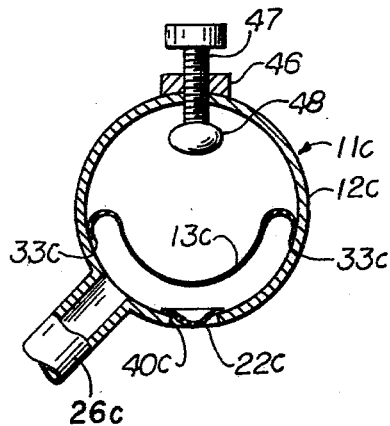
FIG. 14 is a view similar to FIG. 3A of a still further modification.

As an alternative means for adjusting the device to a base volume at which the diaphragm is in firm engagement with the finger or other extremity, it is possible to use the adjusting means illustrated in FIGS. 8, 10 and 14. In FIGS. 8, 9 and 10, adjusting screw 38 is turned so as to tighten annular cuff 11 about the body extremity until the latter is in firm engagement against diaphragm 13 as indicated by the distention of member 22. In such an embodiment, there would be no need to shift sliding scale 23 to the "zero" position, as zero adjustment does not require movement of control means. In FIG. 14, an adjusting screw 47 is used to press the body extremity into firm engagement against the diaphragm 13 rather than by tightening annular cuff 11 about the extremity, with the same effect being achieved as in FIGS. 8 and 10. The body extremity can be suitably cushioned against the base of screw 47 by a cushioning means 48.

In the embodiment shown in FIGS. 1 and 4-6, after adjusting the scale to the "zero" position, the plunger 19 is then moved slowly farther into the cylinder 18 causing the diaphragm 13 to be pressurized and gradually cut off circulation through the digital artery leading to the tip of finger 28. At some point during this increasing pressurizing of the diaphragm, the subject can feel the onset of a slight localized throbbing sensation in the artery inside the cuff 11 which corresponds to the diastolic blood pressure. The location of the end of the plunger 19 relative to the scale marking 24 is the noted. The plunger 19 is further depressed until the subject notes the point in the pressure range at which the localized arterial throbbing stops, which indicates the systolic pressure has been reached and again the marking 24 on the scale 23 with relation to the end of the plunger 19 is noted and this indicates the systolic blood pressure. Preliminary to use of the device, the markings 24 on scale 23 have been calibrated with a standard manometer or calculated with the equations so that direct readings of blood pressure on the indicia 24 are obtainable.

Figure 3:
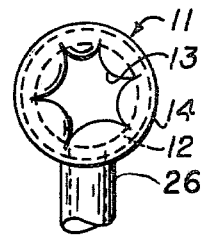
FIG. 3 is an end elevation of the structure of FIG. 2.
Figure 3A:
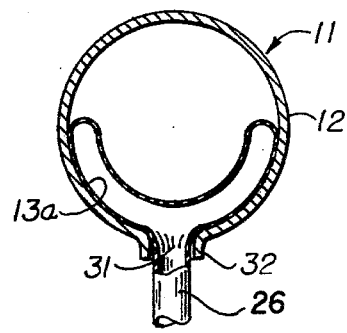
FIG. 3A is a view similar to FIG. 3 and partly broken away in section showing the diaphragm separate from the cuff.

Turning now to the modification of FIG. 3a, the diaphragm 13a is a hollow semicircle in cross section rather than being a hollow circle in cross section as in FIG. 3 and is cemented, or otherwise attached, to rigid casing 12. The opening of the rigid tube 26 into the diaphragm 13a is designated by reference numeral 31 in this modification and a corresponding opening 32 for tube 31 is made in cuff 12. When the plunger (not shown) is depressed in its cylinder, fluid transmitted through the tube 26 creates pressure inside the diaphragm 13a and the finger or other member which has been thrust into the cuff 11 is forced against the rigid wall 12 opposite the diaphragm 13a. In other respects, the structure of FIG. 3A is similar to that of FIGS. 2 and 3 and the same reference numerals are used to designate corresponding parts.

In the modification of FIGS. 8 and 9, the cuff 11a comprises a band 36 similar to that used in a hose clamp. In other words, there is an overlap 37 of the band 36 and the overlap 37 is formed with slots 37a. An adjustment screw 38 engages the slots 37a and is held in place by a screw holder 39. When the screw 38 is turned, it causes the overlap 37 to move relative to the holder 39 so as either to tighten or loosen the cuff 11a, depending upon the direction in which the screw 38 is turned, all as well understood in the hose clamp art.

Diaphragm 13a in this and other modifications may consist of a sheet of relatively flexible materials having turned-in edges 33 cemented or otherwise adhered to the inside of band 36. Thus, there is an air-tight area communicating with tube 26a.

In the modification of FIGS. 8 and 9, an aperture 40 may be formed in the band 36 and a patch 22a of flexible material is cemented or otherwise adhered to band 36 covering aperture 40 so that pressure inside the cuff causes patch 22a to distend out through the aperture 40 in the same manner as the valve-like member 22 of FIG. 1 distends out through a hole in the cylinder 18. In other respects, the modification of FIGS. 8 and 9 resembles that of the preceding modifications and the same reference numerals followed by the subscript a are used to designate corresponding parts.

FIG. 10 is similar in structure to FIGS. 8 and 9 but is simplified. There are two half-casings 41, 42 joined together at a hinge 42a. Opposite hinge 42a each of the casing halves 41, 42 is formed with an outward extending ear 43, one of which is threaded. A screw 38 through the opposite ear is threaded into the aperture and is used to bring the casing halves 41, 42 toward or away from each other to cause pressure on the finger. Diaphragm 13b has its edges attached to casing half 42. In other respects, the modification of FIG. 10 resembles that of FIGS. 8 and 9 and the same reference numerals followed by the subscript b are used to designate corresponding parts.

Directing attention now to the modification of FIG. 14, the casing 12c is solid as in FIG. 3A and diaphragm 13c is similar to that of FIG. 8. On the side of the casing 12c opposite the diaphragm 13c a boss 46 or other means of providing internal threads is located and, threaded into the boss 46, is an adjustment screw 47. Preferably, a piece of soft material 48 is fixed to the inner end of the screw 47. The thumb or other member of the user is inserted in the cuff 12c and by turning the screw 47, the end 48 bears there-against and causes it to exert pressure on the diaphragm 13c. When the valve member 22c (similar to that of FIG. 8) expands through the aperture 40c, that indicates that the zero point has been reached by turning of the screw 47. A plunger and cylinder similar to that of FIG. 1 is then used to pressurize the diaphragm 13c. In other respects, the modification of FIG. 14 resembles that of the preceding modifications and the same reference numerals followed by the subscript c are used to designate corresponding parts.

Note, that in all of these embodiments, the zero-indicating popout member 22, 22a, 22b, 22c may be placed anywhere in the system, be it on the cylinder, as in FIG. 1, or on the cuff, as in FIGS. 8, 10 and 14.

In FIG. 11, the cuff 11 resembles that of any of the preceding modifications. The lower end of the cylinder 18f opens into an enlarged diameter cylinder 51 which functions as a plenum chamber and is connected through opening 52 to the interior of the diaphragm 13f. An opening 53 is formed in the plenum chamber 51 and a valve-like member 22f may project through the opening 53 when the pressure in the diaphragm 13f causes the latter to fit firmly against the exterior of the finger or other member inserted in the cuff 11f.

FIG. 12 differs somewhat from the preceding modifications in that the plunger 19 of FIG. 1 is omitted. A free floating piston 56 slides up and down in the transparent cylinder 18g and its position is controlled by a squeeze bulb 57 attached to the upper end of cylinder 18g. The bulb 57 is squeezed until the valve-like member 22g expands outwardly, indicating that the diaphragm 13g is in contact with the skin of the user. The scale 23g is then zeroed on the position of the free floating piston. Further compression of the bulb 57 causes the piston 56 to move downwardly and the systolic and diastolic pressures are noted as in the preceding modifications.

In FIG. 13, the hollow tapered cone 61 replaces the cylinder of the preceding modifications. Plunger 62 has a ring 63 on its lower edge which engages the inside wall of the cone 61. An annular diaphragm 64 is either fixed on its inner edge to the plunger 62 or slides in air-tight contact and on its outer edge is fixed to the inside wall of the cone 61. In other respects, the modifications of FIGS. 11, 12 and 13 resemble those of the preceding modifications, and the same reference numerals followed by the subscripts f, g, or h, respectively, are used to designate corresponding parts.

Turning now to FIG. 15, a container or casing 66 is provided having a separate plenum chamber 67 formed therein, here shown to be in the upper left hand corner. A cylinder and plunger (not shown) but similar to that of FIG. 1 are connected through the inelastic tubing 17d to the chamber 67. Another tube 26d leads from the chamber 67 to the cuff 11d which may be similar to the cuffs of the other modifications. Formed in the casing 66, so as to be visible from the exterior, is a first opening 68 in which is a valve-like member 69 and a second opening 71 in which is a second valve-like member 72. In the use of the modification of FIG. 15, the finger or other extremity of the user is inserted in the opening in the diaphragm 13d and the piston (not shown) depressed causing pressurization of the plenum chamber 67. When the valve member 69 pops out of the opening 68, the diaphragm 13d is in firm contact with the member of the user and the scale on the cylinder (not shown) is zeroed. The second valve member 72 is of a stiffer material than that of member 69 or in some other way is treated so that it does not pop out at the pressure which activates the valve member 69. Thus, the member 72 is a leak detector. If it does not pop out when a certain pre-selected pressure indicated on the scale of the cylinder is achieved, then the user knows that there is a leak in the system. A one time calibration against a mercury manometer or other pressure gauge is used to determine the pressure at which the member 72 distends. In other respects, the modification of FIG. 15 resembles that of the preceding modifications and the same reference numerals followed by the subscript d are used to indicate corresponding parts.

Figure 16:
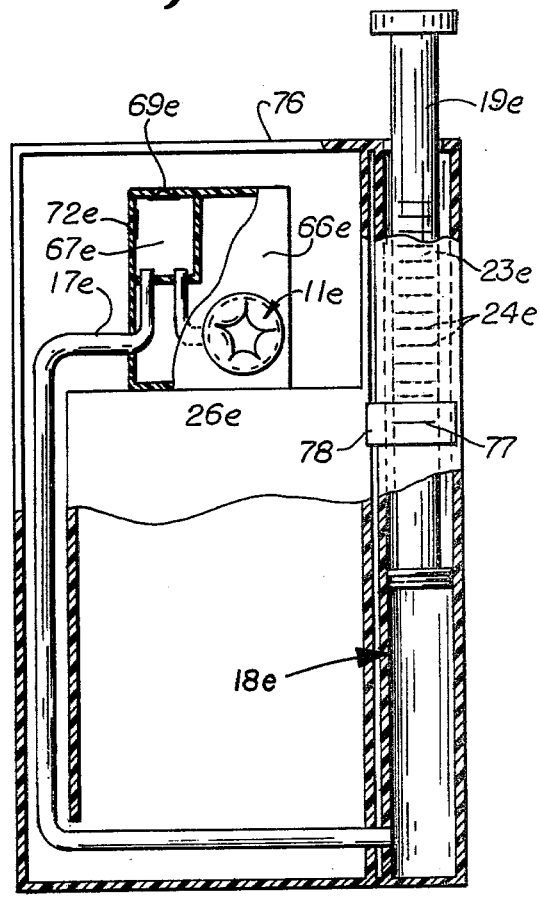
FIG. 16 is a view similar to FIG. 15 showing still another modification in which the entire device, in accordance with the present invention, is installed in a cabinet incorporating the container unit of FIG. 15.

FIG. 16 shows another modification of the casing of FIG. 15. In this modification, the cylinder 18e is enclosed inside the casing 76 and the plunger 19e is depressed vertically along one side of the casing 76. Scale 23e is formed on the plunger 19e. A movable hairline 77 having a flange sliding in vertical slot 78 in casing 76 is set opposite the zero of scale 24e when valve 69e pops out and then is used to read the systolic and diastolic pressures on scale 24e. In this modification, the tube 17e leads to the plenum chamber 67e from cylinder 18e. Casing 66e may be fixed in or detachable from larger casing 76. In the former case, the casing would be positioned so that the members 69e and 72e can be seen from outside the casing 76 through suitable holes therein. In other respects, the modification of FIG. 16 resembles that of the preceding modifications and the same reference numerals followed by the subscript e are used to designate corresponding parts.

It will be understood that a reverse procedure may be followed after "zeroing", namely, the diaphragm is fully pressurized over a range of pressure by depressing plunger 19, the plunger is then slowly withdrawn until the point at which localized arterial throbbing first commences and a reading made of systolic pressure, then the plunger is further withdrawn until the point at which the localized throbbing sensation ends and a reading made of diastolic pressure.

The term "determination of zero" as used herein means determination of the position of the plunger corresponding to some known pressure, namely, that small pressure required to fully inflate or move to a precise position the "zero indicating" device. The magnitude of this pressure is determined by a one-time calibration against a manometer or other means for the particular device or design.

As used herein the term "gaseous" is intended to include those instances wherein the syringe chamber and the diaphragm may include some liquid but the pressurization of the diaphragm is accomplished by compression of gas in accordance with the Perfect Gas Law.

What is claimed is:

1. A device for determining systolic and diastolic blood pressures without the use of a manometer comprising an inelastic cuff to encircle a portion of the subject's body, a inflatable diaphragm on the inside of said cuff inflatable by fluid which is gaseous to affect blood flow through said portion, a tubular member having a first and a second end, duct means communicating from said first end of said tubular member to the interior of said diaphragm, a plunger, the inner end of said plunger fitting through said second end of said tubular member and engaging the internal wall of said member in a fluid-tight manner, whereby depressing said plunger pressurizes said diaphragm to cut off blood flow through said portion of the subject's body, pressure responsive zero-indicating means indicating when said diaphragm firmly engages said portion of the subject's body without affecting blood flow through said portion, and indicia means cooperable with said inner end of said plunger to indicate on said indicia means a zero position in response to said zero-indicating means, said indicia means providing a reading of volume change of fluid caused by said plunger at different positions of said plunger within said tubular member, the position of said plunger in said tubular member determining the pressure in said device in accordance with the Perfect Gas Law and thus usable for determining said pressure at the onset and cessation of Korotkoff phenomena.

2. A device according to claim 1 in which said diaphragm is contained within and is unattached to said cuff.

3. A device according to claim 1 in which said cuff is annular, said annular cuff having adjusting means for bringing the subject's body portion into firm engagement with said diaphragm within said cuff.

4. A device according to claim 3 in which said annular cuff is split into cuff sections, said sections being provided with hinge means and clasp means, allowing said cuff to encircle and be secured around the subject's body portion, said clasp means comprising a portion of said adjusting means.

5. A device according to claim 1 in which said cuff is cylindrical and said diaphragm is a cylinder fitting inside of said cuff and is provided with seal means at opposite ends of said cuff to form an air-tight seal with said cuff, said duct means opening into said cuff intermediate said seal means.

6. A device according to claim 1 in which said tubular member is a cylinder having a sleeve slideable on said cylinder, said indicia means being marked on said sleeve.

7. A device according to claim 1 in which said tubular member is a non-cylindrical tube.

8. A device according to claim 1 in which said tubular member is formed with a vent adjacent its open end so that said plunger may be inserted into said open end up to said vent without inflating said diaphragm.

9. A device according to claim 1 in which said duct means comprises a tube which is flexible but inelastic.

10. A device according to claim 1 wherein a rigid plenum chamber is interposed between said tubular member and said cuff, said chamber communicating with said first end of said tubular member and with said diaphragm.

11. A device according to claim 1 which further comprises a casing, a plenum chamber in said casing, said tubular member, said cuff and said diaphragm being within said casing, said second end communicating with said chamber, said diaphragm communicating with said chamber.

12. A device according to claim 1 further comprising pressure responsive leak detecting means.

13. A method of determining systolic and diastolic blood pressure of a human subject without use of a stethoscope or transducer comprising applying an inflatable diaphragm enclosed in a cuff over a portion of the body of the subject containing an artery, pressurizing said diaphragm until the subject feels a localized throbbing sensation in the artery inside said cuff, measuring the pressure then being applied to the inflated diaphragm as the diastolic blood pressure of the subject, further pressurizing said diaphragm until the localized throbbing sensation terminates, and measuring the pressure then being applied to said diaphragm as the systolic blood pressure of the subject.

14. A method of determining systolic and diastolic blood pressures of a human subject without use of a stethoscope or transducer by the use of an apparatus comprising an inelastic cuff shaped to encircle a portion of the subject's body containing an artery and having a diaphragm on the inside of said cuff inflatable by fluid which is gaseous to affect blood flow through said artery, first means to inflate and pressurize said diaphragm with gaseous fluid, second means to indicate when said diaphragm is in firm contact with said portion without affecting blood flow through said portion, and third means to indicate changes in total volume of fluid in said cuff and said first means, said method comprising:
  a first step of applying said cuff around said portion,
  a second step of actuating said first means until said second means indicates said diaphragm is in firm contact with said portion without affecting blood flow through said portion,
  a third step of further actuating said first means until the subject feels a localized throbbing sensation in the artery within said cuff,
  a fourth step of making a first reading of said third means to read the difference in volume of gaseous fluid in said total volume and thus in accordance with the Perfect Gas Law the difference in pressure in said diaphragm between said second and third steps, said first reading indicating diastolic blood pressure of the subject,
  a fifth step of still further actuating said first means until the throbbing sensation within said cuff terminates and
  a sixth step of making a second reading of said third means to read the difference in volume of gaseous fluid in said total volume and thus in accordance with the Perfect Gas Law the difference in pressure in said diaphragm between said second and fifth steps, said second reading indicating systolic blood pressure of the subject.

15. A method according to claim 14 in which said first means comprises a syringe-like device having a cylinder having a first and an open end and a plunger movable within the second end of said cylinder, said first end being connected to said diaphragm, said third means reading the position of said plunger relative to said zero indicating second means and in which said second step comprises moving said plunger inward of said cylinder, said third step comprises moving said plunger inward of said cylinder a greater distance than said second step and said fifth step comprises moving said plunger inward of said cylinder a greater distance than said third step.

16. A method according to claim 15 in which said third means comprises a sleeve slideable on said cylinder and indicia markings including a zero marking on said sleeve and fourth means responsive to the position of said plunger in juxtaposition to said indicia, and in which said method comprises a seventh step performed after said second step, said seventh step comprising moving said sleeve until said fourth means and said zero marking coincide.

17. A method according to claim 16 in which said second means comprises an aperture in said device and a valve-like member over said aperture, said second step comprising observing when said valve-like member reaches a definite configuration relative to said aperture.

18. A device for determining systolic and diastolic blood pressures of a human subject without use of manometer comprising an inelastic cuff to encircle a portion of the subject's body containing an artery, said cuff including a casing and a diaphragm inside of said casing to engage said body portion, said diaphragm being inflatable by fluid which is gaseous against said body portion to affect blood flow in said artery and thus to effect in the subject a localized throbbing sensation in said artery, a chamber to confine gaseous fluid communicating with said diaphragm for inflating said diaphragm, control means cooperable with said chamber to vary the volume of said chamber thereby varying the gas pressure against said diaphragm, indicator means cooperable with said control means to indicate differences in volume of said chamber between a base volume at which said diaphragm firmly engages said body portion without affecting blood flow through said artery and the highest and lowest volumes at which the subject feels a localized throbbing sensation in said artery, said indicator means thereby providing indications of diastolic and systolic blood pressure at said highest and lowest volumes respectively by providing indications of the changes in volume of said fluid from the base volume in said device and in accordance with the Perfect Gas Law the pressure in said diaphragm.

19. A device according to claim 18 in which said casing wall means are inelastic so that displacement of a volume of fluid by said control means effects an equal volume change in said chamber when said diaphragm is in firm engagement with said body portion.

20. A device according to claim 18 in which said indicator means includes a scale calibrated to indicate pressure in response to volume changes of said chamber, means to adjust the chamber to base volume, means to indicate when said base volume is reached, and means to adjust said indicator to provide a zero reading on said scale at said base volume.

21. A device according to claim 20 in which said casing wall means are inelastic so that displacement of a volume of fluid by said control means effects an equal volume change in said chamber when said diaphragm is in firm engagement with said body portion.

22. A device according to claim 21 wherein said wall means includes a tubular member and a duct connecting one end of said tubular member to said cuff, said control means comprises a plunger movable in the other end of said tubular member in fluid tight relation thereto, and said indicator means is responsive to the movement of said plunger in said tubular member.

23. A method for determining systolic and diastolic blood pressure of a human subject without use of a stethoscope or transducer comprising the steps of applying an inflatable diaphragm enclosed in an inelastic cuff over a portion of the body of the subject containing an artery, variably pressurizing said diaphragm over a range of pressures in which the subject feels a localized throbbing sensation in said artery within said cuff, determining when the pressures of fluid in said diaphragm are at the higher and lower ends of said range by the subject's sensing in said body portion the presence of said throbbing sensation just at each end of said range and the absence of said throbbing sensation just outside of each end of said range, and measuring the pressures in said diaphragm at both ends of said range, the pressure measured at said lower end providing a measure of the diastolic blood pressure of the subject and the pressure measured at said upper end providing a measure of the systolic blood pressure of the subject.

24. A method according to claim 23 in which said diaphragm is variably pressurized by varying the volume of gaseous fluid confined in a closed chamber defined in part by said diaphragm, and said said pressures at the ends of said ranges are observed by measuring changes in the volume of said chamber.

25. A method of determining systolic and diastolic blood pressure of a human subject without use of a stethoscope or transducer comprising the steps of applying an inflatable diaphragm enclosed in a tubular cuff over a portion of the body of the subject containing an artery, confining gaseous fluid in a closed chamber which extends into said cuff to apply gaseous fluid pressure to said diaphragm, varying the volume of said chamber to variably pressurize said diaphragm over a range of pressures in which the subject feels a localized throbbing sensation in said artery within said cuff, determining when the pressures are at the upper and lower ends of said range by the subject's sensing in said body portion the presence of said throbbing sensation just at each end of said range and the absence of said throbbing sensation just outside of each end of said range, measuring the difference between the volume of said chamber when the pressure is at each end of said range and a base volume of said chamber when the diaphragm is in firm contact with said body portion without affecting blood flow through said artery, said volume difference at the lower end of said pressure range providing a measure of the diastolic blood pressure of the subject and said volume difference at the upper end of said pressure range providing a measure of the systolic blood pressure of the subject.

* * * * *